United States Patent [19]

Glajch et al.

[11] Patent Number: 4,746,572
[45] Date of Patent: May 24, 1988

[54] STRUCTURES SURFACE MODIFIED WITH BIDENTATE SILANES

[75] Inventors: Joseph L. Glajch; Joseph J. Kirkland, both of Wilmington, Del.

[73] Assignee: E. I. DuPont de Nemours and Company, Wilmington, Del.

[21] Appl. No.: 936,085

[22] Filed: Nov. 28, 1986

[51] Int. Cl.$^4$ .................. B32B 9/00; B32B 9/04; B01D 15/08; B01J 20/10
[52] U.S. Cl. ................... 428/403; 428/404; 428/405; 428/406; 428/407; 428/447; 55/67; 210/198.2; 210/656; 502/407
[58] Field of Search ................. 428/403–407, 428/447; 55/67, 386; 210/198.2, 656; 502/407, 408; 435/803

[56] References Cited

U.S. PATENT DOCUMENTS

| | | | |
|---|---|---|---|
| 3,722,181 | 3/1973 | Kirkland | 55/67 |
| 3,795,313 | 3/1974 | Kirkland et al. | 210/198 |
| 3,979,546 | 9/1976 | Lewis | 428/394 |
| 4,504,549 | 3/1985 | Pines et al. | 428/447 |
| 4,699,717 | 10/1987 | Riesner et al. | 210/656 X |

OTHER PUBLICATIONS

Snyder and Kirkland ("An Introduction to Modern Liquid Chromatography," Chapter 7, John Wiley and Sons, New York, 1979).
J. Chromatogr., vol. 298, 389–397 (1984).
J. Chromatogr., vol. 352, 199 (1986).
J. Chromagogr., vol. 267, 39 (1983).
Advances in Colloid and Interface Science, vol. 6, 95 (1976).
Deschler et al. (Angew. Chem. Int. Ed. Engl., vol. 25, 236 (1986).
Markiewicz et al. (Nucleic Acids Res., Spec. Publ., vol. 4, 185 (1978).
M. Lalonde et al. (Synthesis, vol. 9, 817 [1985]).
Sindorf et al. [J. Amer. Chem. Soc., vol. 105, 3767 (1983)].

*Primary Examiner*—John E. Kittle
*Assistant Examiner*—Susan S. Rucker

[57] ABSTRACT

A bidentate silane containing at least two silicon atoms bridged by certain groups, arranged to form at least a seven member ring system, is formed between the bidentate silane and the atoms to which the silane is covalently attached on the substrate surface.

27 Claims, 1 Drawing Sheet

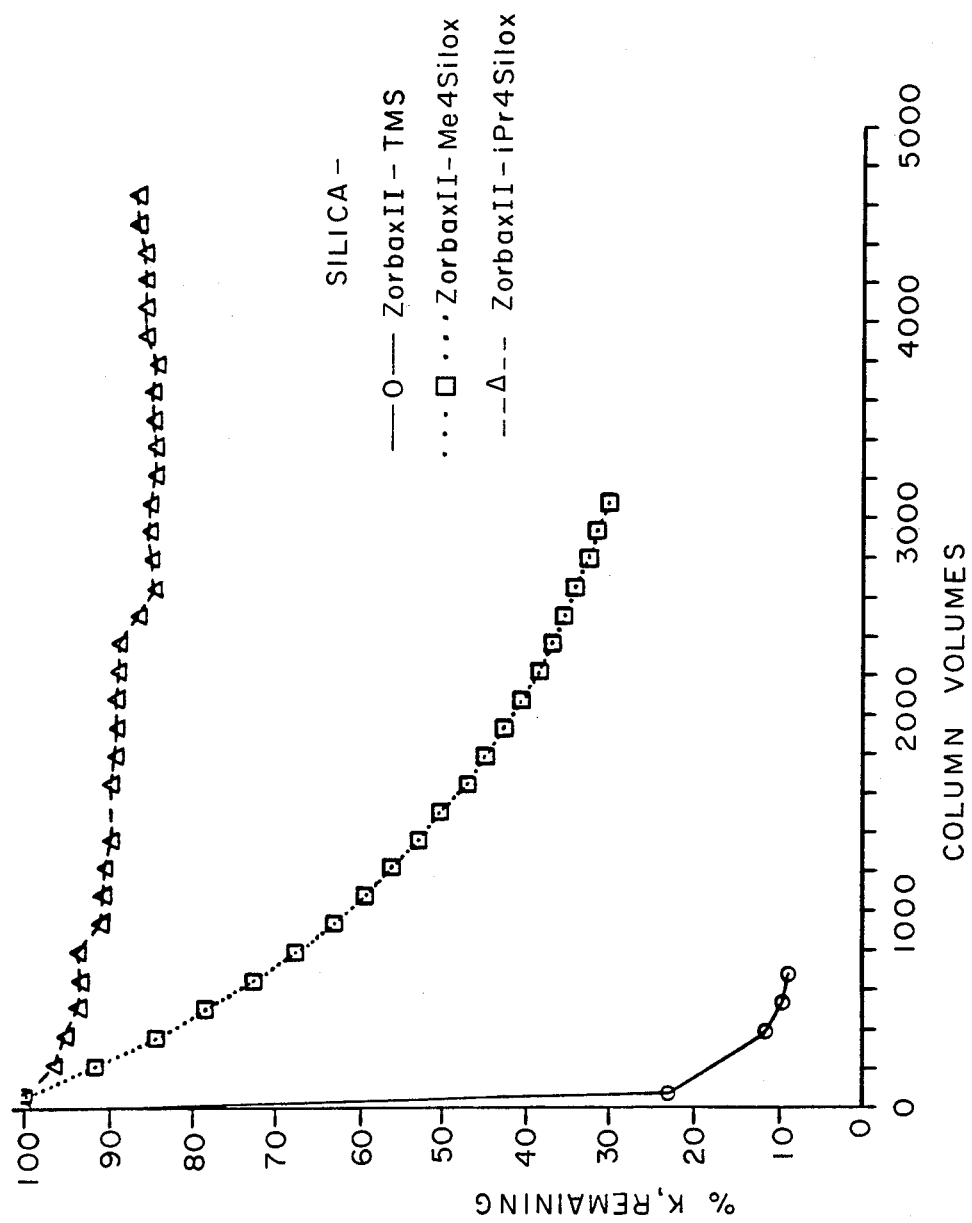

STRUCTURES SURFACE MODIFIED WITH BIDENTATE SILANES

TECHNICAL FIELD

This invention relates to novel compositions comprising a substrate surface modified with bidentate silanes and processes for producing such compositions. The compositions of this invention are useful in a wide variety of applications, including: chromatographic separations, solid-phase synthesis of peptides, proteins and oligonucleotides, and sequencing of peptides and proteins.

BACKGROUND ART

Functionalized supports are useful in many applications, including: chromatography, solid-phase catalysts, solid-phase synthesis of polypeptides and oligonucleotides, and sequencing of polypeptides. The functionality of such supports can, in principle, be a property of the support itself, or more commonly, be the result of the modification of the surface of a substrate. The stability of surface modification is a critical factor whenever that route is chosen. Generally, if the modification is not stable, it means that the modifying reagent is released from the substrate thus contaminating the desired product. In chromatographic applications, this loss of surface modifying reagent is called "bleed". Most prior surface modifying reagents are not stable and their utility has been limited by that instability.

Silanes are the most commonly used surface modifying reagents. Snyder and Kirkland ("An Introduction to Modern Liquid Chromatography," Chapter 7, John Wiley and Sons, New York, 1979) disclose a representative chromatographic support with a surface monolayer of silane. This type of support is limited by the "bleed" of silane exposing the active silica substrate.

Chromatographic supports comprising polymeric silane phases on silica substrates are disclosed by Kirkland et al. (U.S. Pat. No. 3,722,181 and U.S. Pat. No. 3,795,313). These supports are produced using bi- or tri-functional silanes. The silane layers thus formed are relatively thick, limiting mass transfer with resulting poor chromatographic efficiency. Other polymeric silanes phases produced using dimethyl-1,1,4,4-tetramethoxydisilethylene and 1,1,3,3-tetramethyl-1,3-divinyldisilazane are disclosed by Jones et al. [J. Chromatogr., Volume 298, 389–397 (1984)]. The disilethylene reagent has two reactive sites on both Si atoms and can therefore form a polymeric phase with poor chromatographic efficiency. These phases are also limited by lack of control of the polymerization process. The disilazane reagent has only a single reactive site. Single point attachment of silanes to silica can lead to supports with limited stability.

Lork et al. [J. Chromatogr., Vol. 352, 199 (1986)] describe the use of bis-(n-octyldimethylsiloxane) in the preparation of siliceous chromatographic packings. Welsh et al. [J. Chromatogr., Volume 267, 39 (1983)] describe reversed-phase packings for HPLC produced by reacting silica with various disilazanes or disiloxanes. L. Boksanyi et al. [Advances in Colloid and Interface Science, Volume 6, 95 (1976)] used $(CH_3)_3$—Si—O—Si$(CH_3)_3$ to prepare silane-modified silica surfaces. The disiloxanes employed in both references have three alkyl group substituents on each Si atom. These reagents bond to the surface only through a single Si atom. The disilazanes employed contain only a single reactive group again leading to single point attachment and thus limited stability.

Deschler et al. [Angew. Chem. Int. Ed. Engl., Vol. 25, 236 (1986)] discuss silanized siliceous surfaces produced with poly-condensed functionalized silanes from monomers of the type $(RO)_3Si$—$(CH_2)$—X—$(CH_2)_3$—$Si(OR)_3$. These reagents have three reactive groups on each Si atom and, therefore, like the disilethylene of Jones et al., can form polymeric phases with poor chromatographic efficiency.

Pines [EP 129074 A2, Dec. 27, 1984] describes an elastomeric finish to a substrate prepared by reacting a silane and a silanol to obtain a cross-linkable silicone intermediate which is thereafter reacted with a second silanol to obtain a silicone composition. This silicone composition, when catalyzed, can be used as an elastomeric finish on certain solid surfaces. These reagents are not suggested for use in chromatographic systems and since they are highly polymerized, their use in such applications is not advantageous as poor chromatographic efficiency is expected.

R. N. Lewis, U.S. Pat. No. 3,979,546, discloses surfaces that are rendered hydrophobic by the inorganic materials with alpha-alkoxy-omegasiloxanols. These reagents contain two different reactive groups which can react with each other to form undesirable polymeric structures.

Markiewicz et al. [Nucleic Acids Res., Spec. Publ., Volume 4, 185 (1978)] discuss 1,3-dihalo-1,1,3,3-tetraalkyldisiloxane as a silyl-protecting group for 3'—OH and 5'-OH groups of nucleosides. A review of similar reagents for use in protecting certain functional groups of soluble compounds in organic synthesis is given by M. Lalonde et al. [Synthesis, Volume 9, 817 (1985)]. Neither reference discloses using these reagents in any way other than as a protecting group during synthesis of soluble organic compounds.

Sindorf et al. [J. Amer. Chem. Soc., Volume 105, 3767 (1983)] discuss possible structures formed by reaction of bifunctional and trifunctional silanes with silica surfaces. They suggest, that in the presence of water, structures such as the following are formed.

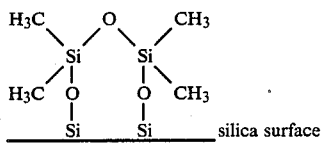

This structure is offered as only one of several present on the silica surface. There is no suggestion that this might be a preferred structure nor is any procedure disclosed for preparing silica substantially completely covered with a silane of such a structure.

There remains a need for highly stable supports for use in chromatography, polypeptide and oligonucleotide synthesis and polypeptide sequencing. These supports should offer a variety of functionalities for use in different applications, be stable during use, and be readily prepared.

SUMMARY OF THE INVENTION

This invention comprises improved support compositions, and processes for preparing said compositions, comprising a substrate, to which is attached a bidentate silane containing at least two silicon atoms bridged by certain groups, so arranged that at least a seven-membered ring system is formed between the bidentate silane and the atoms to which the silane is covalently attached to the substrate surface in the following manner:

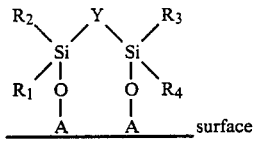

where, $R_1$–$R_4$=alkane, substituted alkane, alkene, substituted alkene, aryl, or substituted aryl; Y=—O—, —CH$_2$—, —CH$_2$CH$_2$—, —(CH$_2$)$_n$—, —(CHZ—CHZ)—, or —(CH$_2$)$_n$CHZ—, where Z=alkane, substituted alkane, alkene, substituted alkene, aryl, substituted aryl, halogen, hydroxyl, hydrogen, nitrile, primary, secondary or tertiary or tetralkylamine, carbonyl, carboxyl, amide, sulfonic acid, nitro, nitroso, sulfonamide, etc., and n=1–6, A are the atoms on the substrate surface to which the silane is covalently attached. The compositions of this invention are prepared by reacting the appropriate bidentate silane reagent with a substrate having reactive surface groups such as —OH or —Cl.

A preferred composition of this invention is prepared from a completely hydrolyzed silica substrate to give a structure as follows:

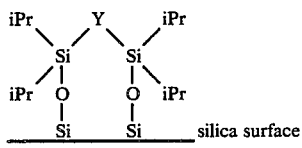

where Y=—O— or —CH$_2$CH$_2$—.

By adjusting the bridge group Y, the distance between the reactive groups on the bidentate silane can be adjusted to closely match the distance between reactive groups on the substrate surface. This matching of the distances between reactive groups allows attachment of substantially all the silane in a bidentate manner. This bidentate attachment provides improved stability of attachment over that possible with monofunctional attachment.

This invention further relates to processes for preparing the compositions described above. These processes comprise reacting a bidentate silane, in which both Si atoms are attached to only one reactive group, with a substrate containing surface-reactive groups so as to bond both Si atoms of substantially all of the silane to the support.

BRIEF DESCRIPTION OF THE DRAWING

The invention may be more easily understood from the following detailed description thereof taken in connection with the accompanying drawing which is a comparison of the stability of the bidentate silanes-isopropyl, methyl and chlorotrimethyl.

DESCRIPTION OF THE INVENTION

Uses for the Invention

The supports of this invention constitute new, efficient, highly-stable media for chromatographic separations. They are especially useful as high-performance liquid chromatography (HPLC) packings for separating biological macromolecules of a wide variety, but particularly those compounds that must be handled in aggressive mobile phases such as those containing trifluoroacetic acid at pH<3. The materials of this invention can be an order-of-magnitude more stable in such environments than those of the prior art, while still providing conditions for optimum retention and column efficiency. Such characteristics are necessary for the reproducible analysis of mixtures, but are especially important for the large-scale or process-scale isolation of purified components. The supports of this invention exhibit characteristics that are in strong contrast to prior HPLC column packings, that show excessive "bleeding" or degradation of the organic stationary phase in such applications. Such degradation results in significant contamination of the isolated product with elements of the "bleeding" or column degradation process. Therefore, the new supports of this invention permit highly superior HPLC separations by reversed- and normal-phase chromatography, ion and ion-exchange chromatography, size-exclusion chromatography, and hydrophobic-interaction chromatography.

Another important use of this invention is in affinity chromatography. The supports of this invention permit highly-efficient affinity separations to be performed on stable, efficient media. One of the present severe limitations in the use of biologically active, covalently-bound affinity exchange groups is the continuous, significant loss or "bleed" of the organic ligand from the packing during use. This process results in decreased loading capacity for the separating medium, and decreased yields that also can result in undesirable non-specific adsorption effects. In addition, the "bleeding" ligand can significantly contaminate the purified product.

The new supports of this invention permit affinity separations to be carried out on silica substrates that have the preferred mechanical properties of strength and optimum pore size, with greatly reduced loss of bound ligand during use. This results in a large increase in the lifetime of the separating medium and a significant increase in the purity of the final product.

The supports of this invention are also useful as catalysts for liquid-phase reactions. Highly-selective organic and organo-metallic ligands can be covalently attached to siliceous or other ceramic supports having optimum mechanical characteristics, to produce stable, active catalysts that have the same desirable long-lifetime and effective properties as those described for the affinity materials above.

The supports of this invention are generally useful whenever highly stable surface modification of a substrate is required to introduce specific functional groups onto said substrate. The functional groups introduced can be used in many ways. A particularly advantageous use is as a point of attachment for substances of biological or synthetic organic interest. Some specific applications are products for the solid-phase synthesis of peptides, proteins, and oligonucleotides. In this application, synthesis of the desired biopolymer is achieved by repetitive addition of individual monomers to the bidentate silane bonded to the substrate. The final biopolymer typically comprises 5 to 50 monomer units and typically is cleaved from the silane before use. The success of these syntheses depends upon many factors, one of which is the chemical stability of the substrate-to-silane bond.

Present materials used in these applications exhibit relatively poor lifetime, causing problems with the reproductibility of results and the necessity for frequent replacement of the solid media used in the synthetic process. The new materials of this invention are especially effective as stable, efficient media in automated peptide, protein, and nucleotide synthesizer instruments. A useful stable modified substrate for such syntheses is:

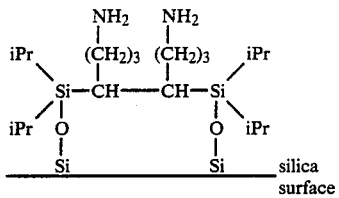

where iPr=isopropyl.

Similarly, the supports of this invention are useful in polypeptide sequencing applications. In this application, the polypeptide to be sequenced is typically adsorbed to a filter disk coated with a non-bonded material such as Polybrene ®, a polymeric quaternary amine. The polypeptide is then subjected to repetitive chemical degradation. A major disadvantage of this approach is that the yields of the repetitive process are poor, at least in part due to loss of the non-bonded coating. Substitution of the supports of this invention would provide a highly stable bonded substrate not suffering many of the difficulties of the prior art. Other applications requiring the specific, stable binding of reagents to a substrate can also benefit from using the supports of this invention.

The Substrate

The substrate, while an important component of the supports of this invention, serves a simple function. It serves as the matrix onto which the bidentate silane is coated. As such, it must provide the necessary shape, rigidity, porosity and other physical characteristics required by a given application. The preferred substrates useful in this invention are solids, as distinguished from liquids or gases. In one embodiment, it can be a metal-oxide or metalloid oxide, but it can be an organic polymer or plastic which will flow under a definite, applied stress. In the most useful embodiments of the novel supports, the substrate will be stable to temperatures of at least 200° C.

The substrate must have a surface that will react with the silane reagents described below. For example, the surfaces of rigid inorganic solids (e.g., silica or chromia) should be hydrolyzed, so that surface —OH groups will be available for reaction with the silane reagent. Alternatively, the surface of these materials can be altered with other appropriate groups that allow reaction with silanes. For example, the surface of carefully dried silica can be chlorinated with thionyl chloride by conventional techniques. This chlorinated surface can then be reacted with bidentate silane reagents containing reactive Si—H or Si—OH groups to prepare the objects of this invention. Preferred metal or metalloid-oxide substrates include chromia and tin oxide, with silica being most preferred.

In some cases, it is desirable to coat the rigid substrate with an appropriate metal or metalloid oxide film that can then be made to react with the appropriate silane reagents. For example, titania can be coated with a thin film of silica according to the methods described by R. K. Iler ("The Chemistry of Silica," John Wiley and Sons, New York, 1979, p. 86). This thin coating of silica can then be hydrolyzed, if necessary, and reacted with the appropriate silane reagent to form the supports of this invention.

A preferred substrate for this invention is silica. This metalloid oxide can be prepared in a variety of shapes and structures to meet many application needs. The silica substrate is especially useful in chromatographic applications, since it can be made in a pure form, in a large range of sizes, and in a variety of porous structures. Examples of silica substrates for chromatography that are useful in this invention are the porous silica microspheres of U.S. Pat. No. 3,782,075 (J. J. Kirkland) and U.S. Pat. No. 4,010,242 (R. K. Iler et al.); the superficially porous article of U.S. Pat. No. 3,505,785 (J. J. Kirkland); the porous silica micrograins of U.S. Pat. No. 4,131,542 (H. E. Bergna et al.), and the surface-stabilized silica of U.S. Pat. No. 4,600,646 (Stout). Such substrates can be used to prepare a variety of supports useful for reversed-phase, ion and ion-exchange, size-exclusion, ion-pair, affinity, and hydrophobic-interaction chromatography.

For the supports of this invention, the surface of metal-oxide and metalloid oxide substrates must be hydrolyzed or in a form which will react with silanes. Silicas that previously have been heated and sintered at temperatures above about 650° C. (the so-called heat strengthened thermally-dehydroxylated silicas) will have little or no SiOH groups on the surface that are required for reaction with appropriate silanes. The surfaces of such dehydroxylated substrates must then be treated, for example by the rehydroxylation procedures of J. Kohler and J. J. Kirkland in U.S. patent application Ser. No. 798,332 (the relevant portion of which is reproduced below) to produce reactive sites for the silanization. The surface of chromia can be hydrated by treatment with an aqueous solution of a reducing agent such as sulfite, as described in British Pat. No. 1,527,760. Alternatively, the metal-oxide or metalloid-oxide can be reacted with other reagents, such as chlorinating agents, to produce surfaces that will react with silane reagents.

The substrate used to prepare the compositions of this invention can also be an organic polymer or plastic. The requirement for this material is that functional groups be present on the surface that can react with the desired silane reagents. An example of such material is the cross-linked polysaccharide, Sepharose (available from Pharmacia Fine Chemicals, Inc., Piscataway, N.J.). This material has a population of —OH groups on the surface that permits reaction with the desired silane reagents. Alternatively, it sometimes is possible to take a normally unreactive polymeric surface and make it reactive towards silane reagents by a chemical etching or "roughening" process. Sometimes this is an oxidative process whereby —OH groups are created by treatment of the polymer with a powerful oxidizing reagent such as peroxides. In some cases, it is possible to create reactive surfaces on certain polymers by treating functional groups on the substrate with a powerful reducing agent such as sodium, to create surface —OH groups that will react with silane reagents.

The substrate must have reactable surface, but the shape and form of the substrate are immaterial. The substrate can be in the form of such diverse shapes as spheres, irregular shaped articles, rods, etc; it can be in the form of plates, films, sheets, fibers, or other massive irregularly shaped objects. The substrate can be porous or non-porous. If porous, where the pores are larger than the reacting silanes, the interior surfaces of the pores will be coated; if the pores are smaller than the reacting silane, only the outside surface of the article will be coated. The choice of substrate will depend upon the ultimate application and will be readily apparent to the skilled artisan.

Rehydroxylation of Silica

In order to use silica as a substrate, rehydroxylation of the silica is often required. For the sake of a complete disclosure, the following section on rehydroxylation of silica is reproduced from U.S. patent application Ser. No. 798,332.

The porous silica microspheres having a total concentration of silanol groups of from about 6 to about 16 $\mu$mol/m$^2$ can be prepared by contacting heat strengthened thermally-dehydroxylated porous silica microspheres with water in the presence of HF or at least one basic activator selected from the group consisting of quaternary ammonium hydroxides, ammonium hydroxide, and organic amines. The contacting normally is conducted at a temperature of from about 25° C. to about 100° C. for sufficient time to generate the desired surface concentration of silanol groups. The strength characteristics of the resulting microspheres are superior to those of the heat-strengthened microspheres. The strength is derived from the inherent integrity of the silica particles based on the optimum ratio of pore volume to silica volume, the calcination pretreatment, and the addition of silica at the contact point of the colloidal particles comprising the microspheres during the rehydroxylation process.

The concentration of silanol groups on a silica surface can be determined in several ways including infrared spectroscopy, solid-state magic angle spinning nuclear magnetic resonance, proton spin counting NMR, and/or thermogravimetric analysis, the latter generally being preferred because of its simplicity and precision. It is noted in this connection that excessive rehydroxylation of a silica surface to greater than about 8 $\mu$mol/m$^2$ of silanol groups will result in silanol groups that are "buried" beneath the silica surface. These groups are detected by TGA, but generally are not available for chromatographic interactions or for reactions with silanizing agents to form bonded-phase packings.

It has been found that activators which promote rehydroxylation to the desired total concentration of silanol groups of from about 6 to about 16 $\mu$mol/m$^2$ are HF and basic activators selected from the group consisting of quaternary ammonium hydroxides, ammonium hydroxide, and organic amines. Preferably, the basic activator is selected from the group consisting of tetraalkylammonium hydroxide, ammonium hydroxides, primary organic amines and secondary organic amines. The relative rate of dissolution of silica by a basic activator can be controlled by maintaining pH in the weakly-basic range. Most primary and secondary organic bases rapidly dissolve silica above a pH of about 10.5. The rate is much slower below this pH value. A basic activator that provides a buffered pH of about 10.5 in dilute solution has desirable properties, especially when hydroxylation is carried out at 25°–50° C. At these temperatures the solubility and the rate of transfer of silica is much lower than at higher temperatures such as 100° C. Preferably, a basic activator is added in a sufficient amount to generate a pH of from about 9 to about 10.5.

For basic activators, the overall rate of attack on the silica surface generally decreases from methyl to ethyl to propyl. For example, normal ethyl-, propyl-, and butylamine, secondary ethyl-propyl- and butylamine are effective activators. Monomethyl- and dimethyl- and dimethylamine can be utilized, if care is exercised. Steric effects appear to have a noticeable influence on the dissolution rate of the silica gel latice as disclosed by A. Wehrli et al. [J. Chromatogr., Volume 149, 199 (1978)]. Methyl amines can be less practical because of their strong tendency to attack silica. Thus, methyl amines are more difficult to control in generating the desired concentration of silanol groups. It has been found that the rate of attack of a base on silica is dependent on the strength (pK$_B$ value), concentration, and geometry of a selected basic activator.

Although tetraalkylammonium hydroxides show strong aggressiveness for dissolving silica, these compounds are preferred basic activators for rehydroxylation. This is the case even though tetramethylammonium, tetrapropylammonium and tetrabutylammonium hydroxide show equal or an even greater tendency than alkali hydroxides to attack the silica surface. Tetraalkylammonium hydroxides are effective activators because at a pH of from about 9 to about 10.5, very little of the free base remains in solution. It is believed that most of the base is absorbed as a monolayer on the silica surface, making the silica somewhat hydrophobic. Hydroxyl ions remaining in solution catalyze the breaking of siloxane groups, while the monolayer of activator on the silica surface retards dissolution and deposition of silica. Therefore, the process can be conveniently interrupted before the degree of hydroxylation passes beyond the desired range.

Ammonium hydroxide is also a preferred basic activator. Dilute ammonium hydroxide at pH 10 reacted with silica for 18 hours and 25° C. is a preferred method for rehydroxylating a silica surface to the desired concentration of silanol groups. Hydrolysis of a 440 m$^2$/g silica by this procedure changed the surface area by only about 25%, and the pore volume of the silica remained essentially unchanged.

Most preferably, the basic activator is at least one primary amine selected from the group consisting of ethylenediamine, n-propylamine and n-butylamine. These amines can generate a pH of from about 9 to about 10.5. A pH in this range accelerates rehydroxylation of the silica surface, without significant change in the surface area and pore diameter of the silica structure as can occur with strong organic bases such as quaternary ammonium hydroxides. When the latter are used as activators, their concentration should be low and the initial pH should not exceed about 10. Secondary amines such as diethyl-, dipropyl-, and dibutylamine are also suitable activators but rehydroxylation reactions are generally slower. Tertiary amines are less preferred activators.

Alkali- or alkaline-earth hydroxides such as NaOH, KOH and CaOH are difficult to control in the rehydroxylation process. Use of these agents can result in significant undesirable changes in the pore structure and surface area of the starting silica. In addition, use of these agents results in an undesired contamination of the starting silica with the cation from the hydroxide. This contamination causes deleterious effects with the silica support in subsequent chromatographic uses.

Acidic solutions of ionic fluorides are also suitable activators. Suitable sources of HF are HF, NH$_4$F and other ionic fluorides not containing a metal or metalloid cation which could deleteriously contaminate the highly purified silica. These activators can be added to an aqueous solution containing thermally dehydroxylated microspheres according to the following procedure. The aqueous solution is adjusted to a pH of about two to about four with a mineral acid such as hydrofluoric, hydrochloric or sulfuric acid. A suitable source of free HF is added to the solution in a concentration that acts as a catalytic agent for the dissolution of the silica surface. The preferred concentration of HF is a function of the surface area of the silica. Preferably, silica microspheres are rehydroxylated in the presence of free HF in a concentration of from about 50 to about 400 ppm. Typically, HF in a concentration of from about 200 to about 400 ppm is suitable to activate the rehydroxylation of a 300–400 m$^2$/g silica. It is believed that fluoride, introduced as HF or an ionic salt thereof at a pH from about 2 to about 4, reacts with a small amount of dissolved silica to form $SiF_6^{-2}$. The $SiF_6^{-2}$ remains in equilibrium with a low concentration of HF. The fluoride ion at low pH functions as an activator to increase the rate of silica hydroxylation.

The Silane Reagents

The bidentate silanes used to prepare the supports of this invention must contain at least two silicon atoms, each containing a monofunctional reactive site. The silicon atoms of the silane also must be bridged by linking groups so arranged that at least a seven-membered ring system is formed between the bidentate silane and atoms of the substrate to which the silane is attached. Thus, the silanes embodied in this invention assume the following structure:

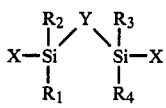

where, X=reactive groups such as chlorine, bromine, iodine, amino, hydroxyl, trifluoroacetoxy, alkoxy, hydrogen, etc.; R$_1$-R$_4$=alkane, substituted alkane, alkene, substituted alkene, aryl, or substituted aryl; Y=—O—, —CH$_2$—, —CH$_2$CH$_2$—, —(CH$_2$)$_n$, —(CHZ-CHZ)— or —(CH$_2$)$_n$CHZ—, where Z is alkane, substituted alkane, alkene, substituted alkene, aryl, substituted aryl, halogen, hydroxyl, hydrogen, nitrile, primary, secondary or tertiary amine, quarternary amine, or tetralkylamine, carbonyl, carboxyl, amide, sulfonic acid, nitro, nitroso, amide, sulfonamide, etc.

The silicon atoms within the silanes of this invention must not be multifunctional, i.e., they must be monofunctional —SiX, and not —SiX$_2$ or —SiX$_3$, since these latter types of reagents will tend to polymerize during preparation of the products of this invention or use, resulting in irreproducible products with different chemical and physical characteristics. A high degree of reproducibility is especially important in chromatographic uses where repeatability of retention is a critical factor. Di- or tri-functional silanes also can only partially react with a surface because of steric problems, leaving reactive groups that can ultimately undergo unwanted reaction with materials being handled. Alternatively, these residual reactive groups can hydrolyze to acidic silanols that can deleteriously interact with the solutes of interest. Since each silicon atom of the bidentate silanes utilized in this invention is monofunctional, it can react only in one configuration, resulting in reproducible surfaces of known structures.

The silanes utilized in this invention can contain a variety of functional groups R$_1$-R$_4$ to fit the intended application. For example, in reversed-phase chromatography carried out in the manner described in Chapter 7 of, "Introduction to Modern Liquid Chromatography," L. R. Snyder and J. J. Kirkland, John Wiley and Sons, New York, 1979, it is desirable for the R$_1$-R$_4$ groups of the silane to consist of alkyl or aryl groups such as C$_1$, C$_3$, C$_4$, phenyl-, phenethyl-, n-C$_8$, n-C$_{18}$ hydrocarbons to enable the desired hydrophobic interaction for retention to occur. For ion-exchange chromatography, the R$_1$-R$_4$ groups can contain groups with ion-exchange functions, for example, —(CH$_2$)$_3$N+(CH$_3$)$_3$Cl$^-$ as an anion-exchanger, and —(CH$_2$)$_3$—C$_6$H$_4$—SO$_3$H as a cation-exchanger. For size-exclusion chromatography, particularly for the separation of highly polar, water-soluble biomacromolecules such as proteins, the surfaces of the substrate are modified with highly polar R$_1$-R$_4$ groups, such as —(CH$_2$)$_3$—O—CH$_2$—CH(OH)—CH$_2$OH, the so-called "diol" function. For hydrophobic interaction chromatography, a weakly hydrophobic stationary phase is desired. For example, a mixed phase of R$_1$, R$_3$=95% "diol" and R$_2$, R$_4$=5% phenethyl groups (—CH$_2$CH$_2$—C$_6$H$_5$). In the case of normal-phase chromatography, polar functional groups are incorporated into the silane as R$_1$-R$_4$ groups, for example, —(CH$_2$)$_3$—NH$_2$ and —(CH$_2$)$_3$—CN.

Said functional groups can be located on the Y bridge group. For example, a "nitrile" stationary phase for normal-phase chromatography can be created by making Y=—CH$_2$—CH([CH$_2$]$_3$—CN) or —CH([CH$_2$]$_3$CN). It is generally preferred to locate said functional groups on the bridge Y group, to allow maximum exposure of the functionality to the solvent. The R$_1$-R$_4$ groups can be chosen to give maximum stability by steric protection against hydrolysis of the SiO bond attached to the substrate.

The substrate can be reacted with a bidentate silane containing appropriately reactive groups such as:

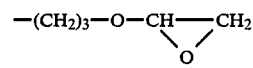

These reactive groups can then be reacted with ligands of specific biological activity to produce affinity supports or other reagents containing desired functionality. For example, an amino group of a protein or peptide can be linked by direct reaction with the epoxide to form structures of the type:

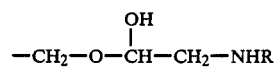

where R=protein or peptide. The epoxide also can be first hydrolyzed to form the "diol" group and then activated with a variety of other reagents prior to reaction with another reagent.

Preferred silanes for products of this invention involve R$_1$-R$_4$ groups that have the steric properties to protect the bonded silane from hydrolysis. These preferred groups include isopropyl, isobutyl, sec-butyl, t-butyl, neo-pentyl, and cyclohexyl with isopropyl and sec-butyl being especially preferred because of the greater convenience and lower cost in preparing the bidentate silanes of interest.

The $R_1$–$R_4$ groups in the silanes used in this invention do not have to be identical. For example, it is sometimes desirable to make the $R_1$–$R_4$ groups a different size so that, because of steric factors, the bidentate silane is spaced on the surface of the substrate so as to provide optimum access to the interacting species of interest. For example, $R_1$ and $R_3$=isopropyl assists in stabilizing the silane against hydrolysis and $R_2$ and $R_4$=$C_{18}$ provides a strong hydrophobic character to the stationary phase for reversed-phase chromatography. By appropriate manipulation of $R_1$ and $R_4$ groups, it also is possible to prepare a material that minimizes the tendency of the stationary phase to denature (cause conformational changes to) biological molecules such as proteins as a result of hydrophobic binding to the stationary phase during separation.

The bridge group of the silanes is a highly important feature of this invention, for it provides a basis for the desired bidentate structure, and a position for introducing reactive or interactive functional groups. However, there are two additional functions of the bridge group that are integral features of this invention. First, the bridge group permits a ring structure of the silane to be formed. This ring structure results in a significantly improved stability of the silane against degradation, for the same reasons that silane ring structures are useful for protecting groups in the synthesis of soluble materials, as described by M. Lalonde et al. [Synthesis, Volume 9, 817 (1985)]. Improvement in bonded silane stability can be at least an order of magnitude in the case of bidentate silanes, compared to commonly used monofunctional or difunctional reagents as described in Chapter 7 of, "Introduction to Modern Liquid Chromatography, L. R. Snyder and J. J. Kirkland (John Wiley and Sons, New York, 1979).

Second, the bridge group allows an appropriate spacing of the reactive groups on the bidentate silane, so that a higher yield of the desired reaction can occur. For example, in the case of the difunctional silane, dichlorodiisopropylsilane, the distance between the reactive chlorine atoms is about 3–3.5 Å. When attempting to react this molecule with fully hydroxylated silica surfaces that has the reactive SiOH groups spaced at as mean distance of about 5.0 Å (R. K. Iler, "The Chemistry of Silica," John Wiley & Sons, New York, 1979, p. 632), only one of the chlorine groups can readily react with the silica surface. Because of the mismatch in bond distances and angles between the other chlorine atom and available adjacent SiOH groups, reaction of the second chlorine is incomplete. This factor results in a residue of chlorine groups on the bonded silane that can deleteriously react with materials of interest, or, in contact with water, hydrolyze to acidic SiOH groups that can act as unwanted adsorption sites.

However, with the bidentate silanes embodied in this invention, because of the structure of the bridge group Y, the reactive atoms on the two silicon atoms can be positioned so that the distance between these reactive atoms more nearly matches the distance between the reacting groups on the solid substrate surface. For example, with dichlorotetraisopropyldisiloxane and dichlorotetraisopropyldisilethylene the distance between the reactive chlorine groups is about 4.5 and 5.0 Å, respectively, which more nearly matches the average distance between SiOH groups on fully hydroxylated silica (about 5 Å). This approximate equivalence in bond distances promotes a very high reaction yield of both chlorine atoms of the bidentate silanes. This has been characterized by $^{29}$Si magic-angle-spinning cross-polarization NMR. Thus, use of an appropriate bridge Y in the bidentate silanes of this invention facilitates the preparation of highly stable, bonded silanes in high yield of the desired bidentate structure.

The bridge group Y on the bidentate silanes used in this invention also can be used to introduce reactive groups that can engage in subsequent reactions to prepare materials of a desired characteristic. For example, Y=—CH(—CH=CH$_2$)—CH(—CH=CH$_2$) provides a reactive group necessary for crosslinking of the bonded silane to other unsaturated monomers or polymers, for example, acrylonitrile to yield nitrile groups on the structure, or polyvinylpyrolidone to produce a highly polar polymeric surface. such polymerization/crosslinking reactions can be carried out using conventional free-radical initiators such as peroxides, or they may initiated by high energy radiation as described by G. Schomburg, et al. [J. Chromatogr., Volume 351, 393 (1986)]. Other useful bridge groups are —CH[(CH$_2$)$_3$NH$_2$]—CH[(CH$_2$)$_3$NH$_2$]; —CH—[(CH$_2$)$_3$—O—CH(OH)CH$_2$—OH]CH[(CH$_2$)$_3$—O—CH(OH)CH$_2$—OH]; —CH[(CH$_2$)$_3$CN]—CH[(CH$_2$)$_3$CN]; and —CH$_2$CH(CH=CH$_2$)CH$_2$. It is understood, of course, that certain of the carbon atoms have an additional bond which attaches to the silicon atoms. For example, the first carbon atom in the first structure listed shows only three substituents. The fourth is the attachment to the silicon atom. These latter bonds are not shown for the sake of clarity. Alternatively, reactive groups to permit polymerization/crosslinking reactions can be attached in the $R_1$–$R_4$ positions of the bidentate silane.

The Reaction

Reaction of the bidentate silanes with the substrate may be carried out under a variety of conditions. Reactions in the vapor phase are less useful than in the liquid phase because of difficulties in obtaining a sufficient vapor pressure of the bidentate silanes, even at elevated temperatures. Thus, vapor-phase reactions can be slow and inconvenient. Normally, the reactions are performed in suitable dry organic solvents, sometimes in the presence of a suitable catalyst or acid acceptor. Finally, reactions sometimes can be performed with the "neat" silane liquid, at elevated temperatures, if required, to increase the reaction rate. A general discussion of the reaction of silanes with the surface of siliceous chromatographic supports is given in Chapter 7 of "An Introduction to Modern Liquid Chromatography", L. R. Snyder and J. J. Kirkland (John Wiley and Sons, New York, 1979). Additional details on the reaction of silanes with porous silicas is found starting on page 108 of "Porous Silica", K. K. Unger (Elsevier Scientific Publishing Co., New York, 1979). General discussions of the reactions of silanes with a variety of materials are given in, "Chemistry and Technology of Silicones", W. Noll (Academic Press, New York, 1968).

It is preferred to perform the reaction in a suitable solvent. In the case of halo-silanes, the reaction is conveniently carried out in a suitable dry organic solvent at elevated temperatures, or at the boiling point of the solvent. Typically, an excess of the silane is used for the reaction, the actual excess depending on the rate of reaction desired. Highly reactive silanes can require only a 20-50% equivalent excess, less reactive silanes can require 2 to 10-fold equivalent excess to produce a high yield of desired covalently-bonded groups in a convenient reaction time.

An acid-acceptor or catalyst is desirable in the reaction of halo-silanes to greatly increase the reaction rate and improve yields of the desired bonded phase. A useful discussion of the role of the basic acid-acceptor and the solvent in the silanization of silicas is given by J. N. Kinkel et al. [J. Chromatogr., Volume 316, 193 (1984)]. The mode of action for these acid-acceptor bases also is postulated in this publication. Typical acid-acceptors useful for the products of this invention include pyridine, triethylamine, 2,6-lutidine, and imidazole. These nucleophile compounds are usually added in excess, typically two-fold excess, relative to the amount of silane used. The rate of reaction of the bidentate silane with the substrate may be slowed if the concentration of acid acceptor is so large that adsorption of this material on the surface of the substrate tends to inhibit access of the reactive silane.

The solvent itself has an important role in the reaction of the silanes of this invention. In the case of monofunctional silanes, it has been postulated by Kinkel et al. (supra) that solvents with both pronounced Lewis acid and Lewis base characteristics (e.g., acetonitrile, dichloromethane, N,N-dimethylformamide) should facilitate the reaction. Such a relationship for bidentate silanes has not yet been established. However, it is clear that the complete reaction of bidentate silanes is slower than monofunctional silanes.

With bidentate halo-silanes, the reactions can be performed in refluxing toluene, xylene or decalin, with pyridine as the acid acceptor. Alternatively, the reaction of halo-silanes may be carried out in a basic solvent such as pyridine. The solvents should be carefully dried to prevent polymerization of the silane, and the reaction should be performed under a blanket of dry inert gas, such as nitrogen. Depending on the silane used, reactions carried out in this manner may require as long as 3-4 days before equilibrium is obtained. Reactions can also be performed in dichloromethane, acetonitrile, and N,N-dimethylformamide, particularly when bases as imidazole and triazole are used as acid acceptors. It is believed that these nucleophiles form intermediates with organohalosilanes, so that the resulting nucleophilic coordination lengthens the Si-X bond to enhance attack on the substrate surface.

Highly reactive silanes such as amino- and trifluoroacetoxysilanes may react faster with siliceous substrates than halosilanes, but comparable yields are achieved if the reactions are allowed to go to completion. Trifluoroacetoxysilanes may be reacted in dichloromethane with 2,6-lutidine as the acid acceptor, according to the procedures described by Corey et al. [Tetrahedron Lett., Volume 22, 3455 (1981)].

Alkoxysilanes react somewhat more slowly with substrates than halo-, amino-, and the other more reactive silanes; consequently, these reactions are conveniently carried out by somewhat different procedures. A preferred procedure for silanizing siliceous substrates is to place the substrate in a flask fitted with a distillation head, add xylene (or toluene), and remove the low-boiling water-organic azeotrope. This step places the system in a very dry state, to insure that the subsequent silanization will proceed in the desired manner. The bidentate alkoxysilane is then added to the flask, either neat or in dry solvent (xylene or toluene), and the flask contents again heated to reflux. The low boiling azeotrope is removed from the refluxing overhead until the boiling point assumes that of the pure solvent or silane, indicating that the reaction is complete. Generally, the reaction of alkoxysilanes with siliceous substrates does not require the addition of acid accepting catalysts, but such materials are useful in some reactions.

The reaction of hydroxysilanes with hydroxylated substrates proceeds with the formation of water as the reaction product. Therefore, reaction conditions used should remove water from the reaction mixture so that the reaction is driven to completion. In this case, reaction solvents can be used that cause a low-boiling azeotrope to be formed. This azeotrope can be removed in much the same manner as described for the alkoxysilane above. Conditions for the reaction must be carefully controlled; otherwise, the bidentate hydroxysilane can react with itself or polymerize, creating undesired reaction products, such as a thick polymer layer on the substrate. One way to minimize polymer formation is to maintain the hydroxysilane concentration at a relatively low level, to encourage reaction of the hydroxysilane with the substrate rather than with itself. In this approach, the reaction can be initiated with a less-than-stoichiometric amount of hydroxysilane, then additional silane is added during the reaction as required to drive the reaction to completion.

Reaction of bidentate silanes with organic hydroxylated polymers proceeds similarly to that for siliceous substrates, except that the selection of solvent and reaction conditions must be adjusted to take into account the nature of the organic polymer. An example of the conditions required can be found in S. Hjertin, et al. [J. Chromatog., Volume 354, 203 (1986)] for the reaction of γ-glycidoxypropyltrimethoxysilane with Sepharose 4B.

The reaction of bidentate silanes with other types of substrates may proceed differently and require modifications in the reaction approach. For example, hydroxylated chromium dioxides show little or no tendency to react with halosilanes. However, such materials react readily with hydrosilanes as described in U.S. Pat. No. 3,939,137. Alternatively, alkoxysilanes can be made to react with chromium dioxide in the manner described in U.S. Pat. No. 4,177,317.

Generally, complete reaction of the bidentate silane with the substrate surface is desired. The level of reaction is largely a function of the population of reactive sites on the substrate and the surface area of the substrate. In the case of fully hydroxylated silica surfaces, about 8 $\mu$mol/m$^2$ of potentially reactive SiOH groups are present on the surface. However, because of the bulk or steric effects associated with the $R_1$-$R_4$ and Y groups of the bidentate silane, all of these SiOH groups cannot be reacted. In the case of smaller reactants, such as dichlorotetramethyldisiloxane, about 2.7 $\mu$mol/m$^2$ of silane can be covalently bonded to the surface. For sterically larger silanes, lower concentrations result. for example, about 1.5 $\mu$mol/m$^2$ of dichlorotetraisopropyldisiloxane can be bonded to a fully hydrolyzed silica surface. However, it is not required that a substrate surface be fully reacted. In some applications, a low to moderate concentration of organic ligand is desired on the surface. To achieve this, the reaction is carried out with a less-than-stoichiometric amount of silane, relative to the amount that would be required for a fully reacted surface. If the bidentate silane contains $R_1$-$R_4$ of larger, highly sterically-protecting groups (e.g., isopropyl), the resulting bonded groups will still exhibit a high degree of stability towards hydrolytic degradation.

Characterization of Products

The configuration of bonded silanes on siliceous products can be characterized by $^{29}$Si and $^{13}$C cross-polarization magic-angle-spinning nuclear magnetic resonance spectroscopy (CP-MAS NMR) and diffuse reflectance infrared Fourier transform spectroscopy (DRIFT). A description of these techniques and their use for characterizing silicas and silane-modified silicas can be found in E. Bayer et al. [J. Chromatogr., Volume 264, 197-213 (1983)] and J. Kohler et al. [J. Chromatogr., Volume 352, 275 (1986)]. By $^{29}$Si CP-MAS NMR, the orientation and bonding characteristics of the various Si atoms has been assigned. We have identified the presence of (1) $R_3$—Si—O—Si, (2) $R_2$—Si(OR)—O—Si, and (3) $R_2$—Si—(O—Si)$_2$ in a bonded phase prepared by reacting a di-n-butyldichlorosilane and tri-n-butyl-chlorosilane with a rehydroxylated silica. The $^{13}$C NMR spectrum shows peaks assignable to all four different carbon atoms in these silanes. The $^{29}$Si NMR spectrum also shows the Si atoms in the solid substrate along with three types of Si atoms of the different silane bonded-phase linkages. The bidentate attachment of the silanes utilized using this technique has been confirmed.

DRIFT spectroscopy can be used to identify the presence or absence of silanols in the modified surfaces of silica. The disappearance of a sharp peak at 3700 cm-1 and the appearance of peaks in the 2800-3000 cm-1 region of the spectra indicate the loss of isolated silanols and the formation of C—H structure due to bonding by the alkyl ligand.

One of the major advantages of the bidentatesilane compositions of this invention is their improved stability compared to conventional monofunctional silanes commonly used in chromatographic packings. This is evident from FIG. 1.

Shown in FIG. 1 is a comparison of the stability of a bidentate silane where $R_1$-$R_4$=isopropyl denoted by the triangles; where $R_1$-$R_4$=methyl denoted by the squares; and chlorotrimethylsilane (TMS) of the prior art denoted by the circles. FIG. 1 displays the level of isocratic retention of 1-phenylheptane exhibited by the column packing (support) (measured as capacity factor k' values—a direct function of the amount of organic silane on the substrate) after subjecting the columns to aggressive water/aceto-nitrile/trifluoroacetic acid (pH=2) mobile phase during gradient elution for known volumes of mobile phase. For these data the same fully hydroxylated silica substrate was used for all preparations. The plots in FIG. 1 clearly show that the rate of degradation of rehydroxylated silica modified with the bidentate dichlorotetramethyldisiloxane (Silica-Me4Silox) is significantly lower than the same substrate modified with the monofunctonal chlorotrimethylsilane (Silica-TMS). We believe that this increased stability of the bidentate silane is because two Si—O—groups attached to the substrate must be broken for loss of the organic ligand to take place, versus only one —Si—O—group for a monofunctional silane. The striking improvement in stability for the bidentate, isopropyl-silane-modified packing over the bidentate, methyl-silane-modified material is due to superior steric protection of the —SiO—groups connected to the silica surface, from hydrolytic degradation. We find that bidentate silanes with phenyl groups in the $R_1$-$R_4$ positions are less stable towards hydrolytic degradation than isopropyl groups, perhaps because of the relatively poor steric protection afforded by the planar phenyl group to the siloxane group attached to the substrate.

EXAMPLE 1

Preparation and Evaluation of a Tetramethyldisiloxane Bonded Phase

Porous silica microspherical particles of seven micron particle size and 300 Å pores were obtained as Zorbax PSM-300 from E. I. du Pont de Nemours and Company (Wilmington, DE). This material was treated by the procedure of J. J. Kirkland and J. Kohler in U.S. Pat. Appl. Ser. No. 798,332 to yield a fully rehydroxylated material with a specific surface area of 52 m$^2$/g as determined by nitrogen adsorption. The specific treatment was as follows:

60 g of PSM-300 silica and 600 mL of 75 ppm HF in water were added to a flask and refluxed at 100° C. for 72 hours. The silica was then washed with 1500 mL of water, 500 mL of acetone, and dried overnight under vacuum (30 Hg). The silica was then placed in 570 mL of water and boiled for 10 h, cooled to room temperature, washed with 500 mL of acetone and dried overnight at 110° C. under vacuum (30 Hg).

Six grams of this material were heated under vacuum (30 in. Hg) at 110° C. to remove adsorbed water, and then placed in a dry nitrogen atmosphere. To this solid substrate was added 60 mL of dry xylene, 240 μL of pyridine, and 4.9 mL of dichlorotetramethyldisiloxane (Cat. No. D4370—Petrarch Systems, Bristol, PA). This mixture was refluxed at 138° C. for 80 hours under a nitrogen purge. The suspension was then cooled and carefully washed with 300 mL each of toluene, methylene chloride, methanol, 50% methanol/water and acetone, and then dried at 110° C. under vacuum (30 in. Hg) overnight. Chemical analysis of the support showed the presence of 0.68% carbon, corresponding to an average surface coverage of 2.7 μmoles/m$^2$ or 5.4 μeq/m$^2$ of bidentate organic silane. Solid-state-magic-angle-spinning $^{13}$C NMR of the material showed the expected single resonance peak at −0.2 ppm for methyl groups on the surface.

Approximately 2 grams of this material was slurry packed into a 0.46 × 15 cm stainless steel tube according to procedures detailed in, "Introduction to Modern Liquid Chromatography", L. R. Snyder, and J. J. Kirkland (John Wiley and Sons, N.Y. 1979, Chapter 5). The resulting chromatographic column was tested using an alternating isocratic/gradient elution solvent system composed of 0.1% trifluoroacetic acid in distilled water (A) and 0.1% trifluoroacetic acid in acetonitrile (B). The solvent was programmed from 0-100% B in 80 minutes, and then isocratic measurements were performed at 50% B using 1-phenylhexane as a test compound. This mobile-phase cycle was repeated for the duration of the column-lifetime studies.

Retention time measurements were made as a function of the number of column volumes of solvent which had passed through the column. The decrease in retention time is a direct measure of the loss of silane bonded-phase from the packing material in the column. For the case of tetramethyldisiloxane-modified silica, this loss was 22% after 500 column volumes (14 hours), compared with a 91% loss for trimethylsilyl-modified silica, prepared using chlorotrimethylsilane and the above procedures.

EXAMPLE 2

Preparation and Evaluation of a Tetramethyldisilethylene Bonded Phase

Reagents and reaction conditions were the same as in Example 1, except that 5.8 grams of tetramethyldichlorodisilethylene (Cat. No. T2015—Petrarch Systems, Bristol, PA) was used as the modifying silane. Elemental analysis on the modified silica showed 0.80% carbon, corresponding to an average surface coverage of 2.1 $\mu$moles/$m^2$ or 4.2 $\mu$eq/$m^2$ of bidentate organic silane. Solid-state-magic-angle spinning $^{13}$C NMR showed two peaks at +9.2 and −1.5 ppm, indicative of the expected methyl and methylene carbons.

A chromatographic column was packed with the support and tested as in Example 1. This column was tested as described in Example 1 and a loss of 41% was found after 500 column volumes of mobile phase was passed through the column. Separation of a mixture of lysozyme, melittin, and ovalbumin was performed with a gradient of 0.1% trifluoroacetic acid/water/acetonitrile. Good separation and peak shape were observed for these compounds, and this separation was maintained even after the 500 volumes of mobile phase had passed through the column.

EXAMPLE 3

Preparation and Evaluation of a Tetraisopropyldisiloxane Bonded Phase

Three grams of silica dried as in Example 1 were mixed with 30 mL of xylene, 120 $\mu$L of pyridine and 4.6 mL of tetraisopropyldichlorodisiloxane (Cat. No. D4368, Petrarch Systems, Bristol, PA). Reaction conditions were as in Example 1, except that the mixture was refluxed for 72 hours. Elemental analysis showed 1.14% carbon, corresponding to 1.5 $\mu$mole/$m^2$ or 3.0 $\mu$eq/$m^2$ of bidentate organic silane. Solid-state-magic-angle-spinning $^{13}$C NMR of the reaction product showed a peak at about +15.6 ppm, as expected for the carbon atoms in this silane.

A chromatographic column was prepared and tested as in Example 1. Loss of retention for phenylheptane was only 6% after purging with 500 column columes of mobile phase. This result compares favorably to the 21% loss in retention for a commercial C4-modified silica (Vydac-214TP, The Separations Group, Hesperia, CA) tested under identical conditions. Continued testing of these two columns showed a 15% loss after 3400 column volumes (96 hours) for the bidentate tetraisopropyldisiloxane-silica, compared with a 35% loss for the Vydac-C4 for the same testing. Elemental analysis of the tetraisopropyldisiloxane-modified silica showed 0.87% carbon remaining on the surface, after testing, or 76% of the original. This correlates well with the 85% residual value suggested by chromatographic retention data.

EXAMPLE 4

Preparation of Divinyldimethyldisiloxane Bonded Phase

Six grams of silica dried as in Example 1 were combined with 60 mL of dry xylene, 202 $\mu$L of pyridine and 2.8 mL of divinyldimethyldichlorodisiloxane (Cat. No. D6206, Petrarch Systems, Bristol, PA). The reaction was performed as in Example 1, except the reflux time was 96 hours. Elemental analysis of the product showed 0.79% carbon, corresponding to 2.2 $\mu$mole/$m^2$ or 4.4 $\mu$eq/$m^2$ of bidentate organic silane.

EXAMPLE 5

Preparation and Evaluation of a Tetraisopropyldisiloxane Bonded Phase

Porous silica microspheres of eight microns in particle size and 150 Å pore size were obtained from E. I. Du Pont de Nemours and Company, Biomedical Products Department, Wilmington, DE, and treated by the procedure of Example 1 (J. J. Kirland and J. Kohler in U.S. Pat. Appl. Ser. No. 798,332) to yield a fully rehydroxylated surface with a specific surface area of 140 $m^2$/g as determined by nitrogen adsorption.

Twenty grams of this substrate was heated at 110° C. overnight under vacuum (30 in. Hg) to remove adsorbed water, and then placed in dry nitrogen atmosphere. To this solid was added 150 mL of dry xylene, 1.8 mL of pyridine, and 35 mL of tetraisopropyldichlorodisiloxane (Cat. No. D4368, Petrarch Systems, Bristol, PA). This mixture was refluxed at 138° C. for 120 hours under a slow nitrogen purge. The suspension was cooled and washed with 300 mL each of toluene, methylene chloride, methanol, 50% methanol/water, and acetone, and then dried at 110° C. under vacuum (30 in. Hg) overnight. The product was refluxed with 60 mL of fresh tetrahydrofuran for 30 minutes and 30 minutes with acetone, and then dried overnight at 110° C. under vacuum (30 in. Hg). Chemical analysis showed 1.38% carbon, corresponding to a surface coverage of 0.68 $\mu$moles/$m^2$ of 1.36 $\mu$eq/$m^2$ of the bidentate silane.

A chromatographic column was prepared of this support and tested as in Example 1. Loss of retention for phenylheptane was only 8% after 13,500 column volumes (132 hours) of continuous testing. Subsequent chemical analysis of the used column material showed 1.32% carbon, corresponding to only a 5% loss in bidentate organic silane as result of the test.

EXAMPLE 6

Preparation of a Tetraisopropyldisiloxane Bonded Phase

Six grams of silica dried as in Example 1 were combined with 60 mL of dry xylene, 390 $\mu$L of pyridine, and 10.84 g of 1,3-dichlorotetraphenyldisiloxane (Cat. No. D4390 Petrarch Systems, Bristol, PA). The reaction was performed as in Example 1. The resulting material was refluxed with 60 mL of fresh dried tetrahydrofuran for 30 minutes and 60 mL of acetone for 30 minutes and dried overnight at 110° C. under vacuum (30 in. Hg). Chemical analysis of the final support showed 1.16% carbon, corresponding to 1.18 $\mu$mole/$m^2$ of 2.36 $\mu$eq/$m^2$ of bidentate silane.

EXAMPLE 7

Preparation of a Tetraisopropyldisiloxane Bonded Phase

Five grams of silica dried as in Example 1 were placed under a dry nitrogen atmosphere, and to this was added 50 mL of pyridine (previously dried with 4A molecular sieve) and 3.28 mL of tetraisopropyldichlorodisiloxane (Cat. No. D4368, Petrarch Systems, Bristol, PA). The mixture was refluxed for 24 hours at 115° C., and the suspension was then cooled and washed with 300 mL each of toluene, methylene chloride, methanol, 50% methanol/water, and acetone. The material was refluxed again with 120 mL of fresh tetrahydrofuran for 30 minutes, then with 120 mL of acetone for 30 minutes, and dried overnight at 110° C. under vacuum (30 in. Hg). Analysis of the final support showed 0.55% carbon, corresponding to 1.12 μmole/m² or 2.24 μeq/m² of silane.

We claim:

1. An improved support comprising a substrate and a bidentate silane attached to the substrate, the bidentate silane containing at least two silicon atoms bridged by certain groups, so arranged that at least a seven-membered ring system is formed in the following manner:

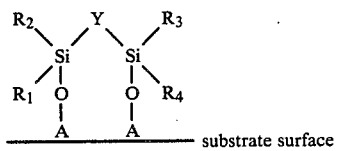
— substrate surface where, $R_1$-$R_4$=alkane, substituted alkane, alkene, substituted alkene, aryl, or substituted arryl; Y=—$CH_2$—, —$CH_2CH_2$—, —$(CH_2)_n$—, —(CHZ—CHZ)—, or —$(CH_2)_n$CHZ—, where Z=alkane, substituted alkane, alkene, substituted alkene, aryl, substituted aryl, halogen, hydroxyl, hydrogen, nitrile, primary, secondary or tertiary or tetralkylamine, carbonyl, carboxyl, amide, sulfonic acid, nitro, nitroso, sulfonamide, etc., n=1-6, and A are the atoms on the substrate surface to which the silane is covalently attached.

2. The support of claim 1 wherein substantially all of the silane is bonded to the substrate through both Si atoms.

3. The support of claim 1 wherein the substrate is a metal-oxide, metalloid oxide or organic polymer or plastic having a surface capable of reacting with bidentate silane reagents.

4. The support of claim 2 wherein the substrate is silica and Y=—O—.

5. The support of claim 1 wherein the substrate is silica and Y=—$CH_2$—$CH_2$—.

6. The support of claim 4 wherein the silica is porous.

7. The support of claim 5 wherein the silica is porous.

8. The support set forth in claim 3 wherein Y=—CH(—CH=$CH_2$)—CH(—CH=$CH_2$); —CH[$(CH_2)_3NH_2$]; —CH[$(CH_2)_3CN$]—CH[$(CH_2)_3CN$]; —CH($C_{18}$)—; —CH—[$(CH_2)_3$—O—CH(OH)$CH_2$—OH]CH[$(CH_2)_3$—O—CH(OH)$CH_2$—OH]; or —CH($C_8$)—CH($C_8$).

9. The support set forth in claim 6 wherein Y=—CH(—CH=$CH_2$)—CH(—CH=$CH_2$); —CH[$(CH_2)_3NH_2$]; —CH[$(CH_2)_3CN$]—CH[$(CH_2)_3CN$]; —CH($C_{18}$)—; —CH—[$(CH_2)_3$—O—CH(OH)$CH_2$—OH]CH[$(CH_2)_3$—O—CH(OH)$CH_2$—OH]; or —CH($C_8$)—CH($C_8$).

10. The support set forth in claim 7 wherein Y=—CH(—CH=$CH_2$)—CH(—CH=$CH_2$); —CH[$(CH_2)_3NH_2$]; —CH[$(CH_2)_3CN$]—CH[$(CH_2)_3CN$]; —CH($C_{18}$)—; —CH—[$(CH_2)_3$—O—CH(OH)$CH_2$—OH]CH[$(CH_2)_3$—O—CH(OH)$CH_2$—OH]; or —CH($C_8$)—C($C_8$).

11. The support set forth in claim 1 which is made by reacting a bidentate silane reagent with the substrate which contains reactive surface groups.

12. The support set forth in claim 11 wherein the reactive surface groups include —OH or —Cl.

13. The support set forth in claim 11 wherein the reactive surface groups are established by hydroxylating the surface of the substrate.

14. The support of claim 1 used for chromatographic separations.

15. The support of claim 6 used for chromatographic separations.

16. The support of claim 7 used for chromatographic separations.

17. The support of claim 11 wherein the silicon atoms of the bidentate silane are monofunctional.

18. An improved support according to claim 1 wherein the $R_1$-$R_4$ groups provide steric protection of the bonded silane from hydrolysis.

19. The support set forth in claim 18 wherein $R_1$-$R_4$ are isopropyl, secondary butyl, isobutyl, t-butyl, neopentyl, or cyclohexyl.

20. The support set forth in claim 6 wherein $R_1$-$R_4$ are isopropyl, isobutyl, t-butyl or neopentyl.

21. The support set forth in claim 7 wherein $R_1$-$R_4$ are isopropyl, isobutyl, t-butyl or neopentyl.

22. The support set forth in claim 9 wherein $R_1$-$R_4$ are isopropyl, isobutyl, t-butyl or neopentyl.

23. The support set forth in claim 10 wherein $R_1$-$R_4$ are isopropyl, isobutyl, t-butyl or neopentyl.

24. The support set forth in claim 1 wherein Y is selected to provide a spacing between the two reactable atoms of the bidentate silane comparable to that of the attachment points on the substrate.

25. An improved support comprising a silica substrate and bidentate silane attached to the substrate, the bidentate silane containing at least two silicon atoms bridged by certain groups, so arranged that at least a seven membered ring systems is formed to have the structure:

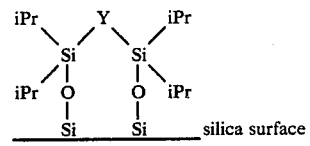

where Y=—O— or —$CH_2CH_2$—.

26. The support set forth in claim 25 which is made by reacting a bidentate silane reagent with the substrate which contains reactive surface groups.

27. The support set forth in claim 26 wherein the reactive surface groups include —OH or —Cl.

* * * * *